United States Patent
Kandel et al.

(10) Patent No.: US 10,159,959 B2
(45) Date of Patent: *Dec. 25, 2018

(54) TEMPLATED ACTIVE MATERIAL

(71) Applicant: ExxonMobil Chemical Patents Inc., Baytown, TX (US)

(72) Inventors: Kapil Kandel, Humble, TX (US); Paul F. Keusenkothen, Houston, TX (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/905,282

(22) Filed: Feb. 26, 2018

(65) Prior Publication Data
US 2018/0178199 A1    Jun. 28, 2018

Related U.S. Application Data

(62) Division of application No. 15/146,433, filed on May 4, 2016, now Pat. No. 9,931,616.

(60) Provisional application No. 62/167,525, filed on May 28, 2015.

(30) Foreign Application Priority Data

Jul. 22, 2015 (EP) ..................... 15177842

(51) Int. Cl.
| | |
|---|---|
| *C07C 29/50* | (2006.01) |
| *C07C 29/153* | (2006.01) |
| *C10G 2/00* | (2006.01) |
| *B01J 23/745* | (2006.01) |
| *B01J 23/72* | (2006.01) |
| *B01J 37/02* | (2006.01) |
| *B01J 37/00* | (2006.01) |
| *B01J 37/06* | (2006.01) |
| *B01J 23/89* | (2006.01) |
| *B01J 23/80* | (2006.01) |
| *B01J 23/00* | (2006.01) |
| *B01J 23/889* | (2006.01) |
| *B01J 37/08* | (2006.01) |
| *B01J 35/10* | (2006.01) |
| *B01J 37/16* | (2006.01) |
| *B01J 29/03* | (2006.01) |
| *B01J 21/08* | (2006.01) |

(52) U.S. Cl.
CPC .......... *B01J 23/745* (2013.01); *B01J 23/002* (2013.01); *B01J 23/72* (2013.01); *B01J 23/80* (2013.01); *B01J 23/8892* (2013.01); *B01J 23/89* (2013.01); *B01J 35/1014* (2013.01); *B01J 35/1019* (2013.01); *B01J 35/1061* (2013.01); *B01J 37/0018* (2013.01); *B01J 37/0203* (2013.01); *B01J 37/0205* (2013.01); *B01J 37/0215* (2013.01); *B01J 37/06* (2013.01); *B01J 37/08* (2013.01); *B01J 37/086* (2013.01); *B01J 37/16* (2013.01); *C07C 29/153* (2013.01); *C07C 29/50* (2013.01); *C10G 2/332* (2013.01); *B01J 21/08* (2013.01); *B01J 29/0333* (2013.01); *B01J 2229/18* (2013.01); *B01J 2229/38* (2013.01)

(58) Field of Classification Search
CPC .... C07C 29/156; C07C 31/125; B01J 23/745; B01J 35/1019; B01J 8/02; B01J 35/1014; B01J 2208/027

See application file for complete search history.

(56) References Cited

U.S. PATENT DOCUMENTS

| | | |
|---|---|---|
| 4,122,110 A | 10/1978 | Sugier et al. |
| 6,096,288 A | 8/2000 | Roith |
| 2004/0192989 A1 | 9/2004 | Espinoza et al. |
| 2005/0107481 A1 | 5/2005 | Janssen et al. |
| 2007/0259972 A1 | 11/2007 | Lattner et al. |
| 2008/0033218 A1 | 2/2008 | Lattner et al. |

OTHER PUBLICATIONS

Cao et al., "Mesoporous CuO—Fe2O3 composite catalysts for low-temperature carbon monoxide oxidation", Applied Catalysis B: Environmental, vol. 79, (2008) pp. 26-34.

Frennet, et al., "Long-chain alcohols from syngas", In Studies in Surface Science and Catalysis A. Corma, F.V.Melo, S. Mendioroz and J.L.G. Fierro, Eds., Elsevier Science 2000, vol. 130, pp. 3699-3704.

Xiang et al., "Long-Chain Terminal Alcohols through Catalytic CO Hydrogenation", Journal of the American Chemical Society, 2013, vol. 135, pp. 7114-7117.

Beck J.S., et al., J. Am. Chem. Soc., vol. 114, No. 127, 10834-10843 (1992).

Cao, at al., J. Mater. Sci. (2009) 44:6663-6669.

Guilong et al. "Nanoparticles of Cu-Co Alloy Supported on High Surface Area LaFeO 3—preparation and catalytic performance for higher alcohol synthesis from syngas", RSC Advances: An international Journal to Further the Chemical Sciences, vol. 5, No. 40, Mar. 26, 2015 pp. 31637-31647.

Jiao F., et al., J. Mater. Chem, A, 2, 3065-3071 (2014).

Liu Q., et al., Microporous and Mesoporous Materials, 100, 233-240 (2007).

Lu, et al., ChemCat Chem 2014, 6, 473-478.

(Continued)

*Primary Examiner* — Jafar F Parsa

(57) ABSTRACT

The invention relates to templated active material, including those deriving order from organic and/or inorganic templating agents. The invention also relates to methods for producing templated active material, and to active material produced by such methods, and the use of such templated active material for producing oxygenate.

5 Claims, No Drawings

(56) References Cited

OTHER PUBLICATIONS

Lu, et al., Applied Catalysis A: General 429-430 (2012).
Maerle et al. "Structured mesoporous Mn, Fe, and Co oxides: Synthesis, Physiochemical, and Catalytic Properties", Russian Journal of Physical Chemistry A., vol. 88, No. 2, Feb. 1, 2014, pp. 238-242.
Sakarnoto, et al., Nature, 408, 449-452 (2000).
Schwickardi M. et al. "High Surface-Area Oxides Obtained by an Activated Carbon Route", Chemistry of Materials, American Chemical society, US. vol. 14, No. 9, Sep. 1, 2002, pp. 3913-3919.
Yoshimura T., et al., Langmuir 28, 9322-9331 (2012).
Gao et al., "Catalytic conversion of syngas to mixed alcohols over CuFe based catalyst derived from layered double hydroxides", Catalysis Science and Technology, 2013, vol. 3, pp. 1324-1332.
Kustrowski et al., "Modification of MCM-48, SBA-15-, and MSY-type mesoporous silicas with transition metal oxides using the molecular designed dispersion method", Journal of Physical Chemistry B, 2005, vol. 109, pp. 11552-11558.

TEMPLATED ACTIVE MATERIAL

PRIORITY

This application is a divisional of and claims priority to and the benefit of U.S. patent application Ser. No. 15/146,433, filed May 4, 2016, U.S. Patent Application Ser. No. 62/167,525, filed May 28, 2015, and European Patent Application No. 15177842.0 filed Jul. 22, 2015, all of which are herein incorporated by reference. The following related cases are also incorporated by reference in their entireties: U.S. Provisional Patent Application Ser. No. 62/167,514, filed May 28, 2015 and European Patent Application No. 15183246.6 Sep. 1, 2015.

FIELD OF THE INVENTION

The invention relates to templated active material, including those deriving order from organic and/or inorganic templating agents. The invention also relates to methods for producing templated active material, and to active material produced by such methods, and the use of such templated active material for producing oxygenate.

BACKGROUND OF THE INVENTION

Many commercially important compositions, including fuel, lubricating oil, detergent, and plasticizer compositions, contain or are produced using oxygenate such as long chain alcohol (unbranched $C_{4+}$ alcohol having one terminal hydroxyl). Butanol, for example, can be used to produce butyl acrylate and methacrylate. $C_5$ alcohol can be used to produce lubricating oil additives such as zinc diamyldithiophosphate. Alcohols in the $C_6$-$C_9$ range can be used to produce plasticizer. $C_6$-$C_9$ alcohol, particularly $C_{12}$-$C_{15}$ alcohol, can be used to produce detergent, typically by first converting the alcohol to alcohol sulfate, ethoxylate, alcohol ether sulfate, or fatty amine.

One way to produce long chain alcohol is by catalytic hydroformylation of olefin to produce a reaction product comprising aldehyde, separating linear aldehyde from the reaction product, and then hydrogenation of the linear aldehyde. The hydroformylation reaction is carried out by contacting the olefin with a mixture of carbon monoxide and molecular hydrogen in the presence of at least one hydroformylation catalyst. Conventional hydroformylation catalysts typically comprise at least one metal selected from Groups 8-10 of the Periodic Table, especially at least one metal selected from Group 9, such as one or more of cobalt, rhodium, and iridium. Although rhodium and iridium exhibit greater hydroformylation activity, cobalt is typically used to lessen costs. When using a cobalt catalyst such as HCo(CO)$_4$, hydroformylation conditions typically include a temperature $\geq 140°$ C. and a pressure $\geq 24$ MPa. Relatively high pressure is needed for at least two reasons. First, high total pressure is needed to stabilize the catalyst at the reaction temperature. Second, selectivity for the desired linear aldehyde over branched aldehyde by-product increases with increasing carbon monoxide partial pressure.

Besides the relatively high temperature and pressure needed, conventional hydroformylation processes are also sensitive to the type of olefin present in the feed. Linear olefin is approximately an order of magnitude more reactive for producing the desired aldehyde than is iso-olefin having the same number of carbon atoms. Consequently, conventional hydroformylation processes typically require concentrating linear olefin in the feed, e.g., by separating and conducting away any isoolefin. In addition to these difficulties, catalysts such as HCo(CO)$_4$ have a normal boiling point similar to that of desirable linear aldehydes, which increases the complexity of product and catalyst recovery stages.

In order to more easily recover catalyst from the long-chain alcohol, processes have been developed to produce long chain alcohol by direct hydration of 1-alkene using acids, metal oxides, zeolites, or clays. One difficulty in operating these processes results from an aspect of Markovnikov's rule: a proton bonds to a hydrocarbon molecule at the molecule's least-substituted carbon atom. Accordingly, the hydration reaction protonates the 1-alkene's double bond, which disfavors transition states amenable to long chain alcohol formation. Although triple-relay, platinum-ruthenium catalyst systems having anti-Markovnikov behavior have been developed for 1-alkene hydration, a more recent approach involves the direct production of long chain alcohol by a modified Fischer-Tropsch ("FT") synthesis.

As reported in Lu, et al., ChemCat Chem 2014, 6, 473-478, processes using a templated Cu—Fe FT synthesis catalysts can be operated to strongly favor producing long chain alcohol (anti-Markovnikov behavior) from a carbon monoxide—molecular hydrogen mixture over producing branched alcohol having the same number of carbon atoms (Markovnikov behavior). The reference discloses reacting a 1:1 molar ratio carbon monoxide—molecular hydrogen mixture in the presence of a three-dimensional, ordered macroporous catalyst comprising CuO and Fe$_3$O$_4$. The reaction is carried out at a temperature of 240° C. and a pressure of 700 psi (approximately 4.8 Mpa). The reference discloses a selectivity to $C_{2+}$ 1-alcohol production of 40% (weight basis) and a feed carbon monoxide conversion of 45% (weight basis). 1-alcohols in the reaction product have a number of carbon atoms in the range of from 1 to 16, with a weight average of about 9, resulting in an Anderson-Shulz-Flory Chain Growth Probability ("α") of 0.74.

Catalysts are now desired for processes which produce oxygenate such as long chain alcohol from a carbon monoxide—molecular hydrogen mixture, the process having a feed carbon monoxide conversion >45% (weight basis) and a selectivity to oxygenate such as 1-alcohol >40% (weight basis). Catalysts are particularly desired which are effective for catalytically converting syngas to oxygenate at a reaction temperature $\leq 250°$ C. and a total pressure $\leq 5$ MPa.

SUMMARY OF THE INVENTION

In certain aspects, the invention relates to a process for producing oxygenate, such as long chain alcohol, from a mixture of carbon monoxide and molecular hydrogen. The process can be carried out a reaction temperature $\leq 250°$ C. and a total pressure $\leq 5$ Mpa, and when operated under those conditions has at least one of (i) a feed carbon monoxide conversion >45% (weight basis), (ii) an oxygenate selectivity >40% (wt. basis), such as a 1-alcohol selectivity >40%, and (iii) α>0.74. Other oxygenate, e.g., aldehyde of equivalent chain length to the long chain alcohol, can be produced by dehydrogenating the long chain alcohol.

The invention is based in part on the discovery of templated mesoporous active materials, which when utilized as catalepsy in processes for making oxygenate from carbon monoxide and molecular hydrogen have increased activity and selectivity for oxygenate production over conventional catalysts.

In certain aspects, the invention relates to a templated active material comprising a first metal $M_1$ and $\geq 0.5$ wt. % of a second metal $M_2$ that is not the same as $M_1$. $M_1$ and $M_2$ each include at least one metal selected from Groups 7-12 of the Periodic Table. The templated active material comprises ≤1.0 wt. % of oxide of $M_1$ and ≤1.0 wt. % of oxide of $M_2$. The templated active material has an $M_2$ to $M_1$ molar ratio in the range of from 0.1 to 10. The templated active material also has a plurality of pores having an average pore size in the range of from 2 nm to 50 nm, and an average surface area ≥50 $m^2/g$.

In other aspects, the invention relates to a method for making a templated active material which derives structure from a mesoporous inorganic template comprising oxide of silicon. The process includes substituting a first metal $M_1$ for ≥10 wt. % of the oxide's silicon to produce a metal-substituted template, wherein $M_1$ includes at least one metal selected from Groups 7-12 of the Periodic Table. The metal-substituted template is calcined under conditions which include exposing the metal-substituted template to an oxidant at a temperature ≥350° C. The method includes removing ≥90 wt. % of any silicon in the calcined metal-substituted template to form a mono-metallic templated precursor. A multi-metallic templated precursor is produced by depositing ≥0.5 wt. % of a second metal $M_2$ on and/or in the monometallic templated precursor, wherein (i) $M_2$ is not the same as $M_1$, (ii) $M_2$ includes at least one metal selected from Groups 7-12 of the Periodic Table, and (iii) the multi-metallic templated precursor has an $M_2$ to $M_1$ molar ratio in the range of from 0.1 to 10. The multi-metallic templated precursor is calcined under conditions which include exposing the a multi-metallic templated precursor to an oxidant at a temperature ≥350° C., and the templated active material is produced by reducing the calcined multi-metallic templated precursor.

Other aspects of the invention relate to another method for making a templated active material deriving structure from a mesoporous inorganic template comprising oxide of silicon. It differs from the preceding method in that the silicon removal is carried out after depositing the second metal. Accordingly, the method includes substituting a first metal $M_1$ for ≥10 wt. % of the oxide's silicon to produce a metal-substituted template, wherein $M_1$ includes at least one metal selected from Groups 7-12 of the Periodic Table, and then calcining the metal-substituted template under conditions which include exposing the metal-substituted template to an oxidant at a temperature ≥350° C. A multi-metallic template having an $M_2$ to $M_1$ molar ratio in the range of from 0.1 to 10 is produced by depositing ≥0.5 wt. % of a second metal $M_2$ on and/or in the calcined the metal-substituted template. $M_2$ is not the same as $M_1$, and $M_2$ includes at least one metal selected from Groups 7-12 of the Periodic Table. A multi-metallic templated precursor is produced by removing ≥90 wt. % of any silicon in the multi-metallic template, which is then calcined under conditions which include exposing the multi-metallic templated precursor to an oxidant at a temperature ≥350° C. to produce the templated active material.

Other aspects of the invention relate to yet another method for making a templated active material deriving structure from a mesoporous inorganic template comprising oxide of silicon. The method differs from the preceding aspects in that the first and second metal are substituted for the oxide's silicon in a single step to produce a multi-metallic substituted template. More particularly, the method includes substituting a first metal $M_1$ for ≥10 wt. % of the oxide's silicon and substituting a second metal $M_2$ for ≥10 wt. % of the oxide's silicon, wherein (i) $M_1$ includes at least one metal selected from Groups 7-12 of the Periodic Table, (ii) $M_2$ includes at least one metal selected from Groups 7-12 of the Periodic Table, (iii) $M_2$ is not the same as $M_1$, and (iv) the multi-metallic substituted template has an $M_2$ to $M_1$ molar ratio in the range of from 0.1 to 10. The method further includes removing ≥90 wt. % of any silicon in the multi-metallic substituted template to form a multi-metallic templated precursor, and calcining the multi-metallic templated precursor under conditions which include exposing the multi-metallic templated precursor to an oxidant at a temperature ≥350° C. The templated active material is produced by reducing the calcined multi-metallic templated precursor.

Other aspects of the invention relate to yet another method for making a templated active material. The method differs from the preceding aspects in that the templated active material derives structure from a carbonaceous structure-directing agent, which lessens the need for a silicon-removal step. The method includes producing a mesoporous oxide template by reacting a template synthesis mixture comprising the carbonaceous structure-directing agent with nitrate of a first metal $M_1$ and nitrate of a second metal $M_2$ that is not the same as $M_1$. $M_1$ and $M_2$ each include at least one metal selected from Groups 7-12 of the Periodic Table. $M_2$ includes at least one metal selected from Groups 7-12 of the Periodic Table. The mesoporous oxide template, which has an $M_2$ to $M_1$ molar ratio in the range of from 0.1 to 10, is then calcined to produce a multi-metallic templated precursor. The calcining is carried out under conditions which include exposing the mesoporous oxide template to an oxidant at a temperature ≥350° C. The templated active material is produced by reducing the calcined multi-metallic templated precursor.

Other aspects of the invention relate to yet another method for making a templated active material deriving structure from a carbonaceous structure-directing agent. The method differs from the preceding aspects in that the template synthesis mixture comprises a carbonaceous structure-directing agent and nitrate of a first metal $M_1$, but not nitrate of a second metal $M_2$. Reacting the synthesis mixture produces a mesoporous oxide template. A mono-metallic templated precursor is produced by calcining the mesoporous oxide template under conditions which include exposing the mesoporous oxide template to an oxidant at a temperature ≥350° C. A second metal $M_2$ is then deposited on and/or in the monometallic templated precursor in an amount ≥0.5 wt. %, to produce a multi-metallic templated precursor, wherein (i) $M_2$ is not the same as $M_1$, (ii) $M_2$ includes at least one metal selected from Groups 7-12 of the Periodic Table, and (iii) the multi-metallic templated precursor has an $M_2$ to $M_1$ molar ratio in the range of from 0.1 to 10. The multi-metallic templated precursor calcining is calcined under conditions which include exposing the multi-metallic templated precursor to an oxidant at a temperature ≥350° C. The templated active material is produced by reducing the calcined multi-metallic templated precursor.

Other aspects of the invention relate to the templated active material product of any of the preceding methods.

Other aspects of the invention relate to a process for producing oxygenate from a feed mixture comprising molecular hydrogen and ≥0.01 wt. % of carbon monoxide, wherein the feed mixture has a molecular hydrogen to carbon monoxide molar ratio in the range of from 0.01 to 100. The feed mixture's carbon monoxide and molecular hydrogen are reacted in the presence of at least one templated active material of any of the preceding aspects. The reaction is carried out at a temperature ≥150° C., a total pressure ≥0.8 MPa (about 100 psig), and a space velocity (GHSV) ≥100 hr$^{-1}$. The reaction effluent comprises any unreacted feed mixture and a reaction product which includes oxygenate such as long chain alcohol.

DETAILED DESCRIPTION OF THE INVENTION

Definitions

For the purpose of this description and appended claims, the following terms are defined:

The term "$C_n$" hydrocarbon means hydrocarbon having n carbon atom(s) per molecule, wherein n is a positive integer. The term "$C_{n+}$" hydrocarbon means hydrocarbon having at least n carbon atom(s) per molecule, wherein n is a positive integer. The term "$C_{n-}$" hydrocarbon means hydrocarbon having no more than n number of carbon atom(s) per molecule, wherein n is a positive integer. The term "hydrocarbon" means a class of compounds containing hydrogen bound to carbon, and encompasses (i) saturated hydrocarbon, (ii) unsaturated hydrocarbon, and (iii) mixtures of hydrocarbons, including mixtures of hydrocarbon compounds (saturated and/or unsaturated), including mixtures of hydrocarbon compounds having different values of n.

The term "$C_n$" alcohol means alcohol having n carbon atom(s) per molecule, wherein n is a positive integer. The term "$C_{n+}$" alcohol means alcohol having at least n carbon atom(s) per molecule, wherein n is a positive integer. The term "$C_{n-}$" alcohol means alcohol having no more than n number of carbon atom(s) per molecule, wherein n is a positive integer. The term "oxygenate" means a class of compounds which include at least one oxygen atom, e.g., alcohol and ether. The term "alcohol" means a class of compounds which include at least one aliphatic carbon bound to a hydroxyl group, but excluding aldehyde, ketone, and carboxylic acid. The term alcohol encompasses (i) saturated and unsaturated alcohol, (ii) alcohol having one hydroxyl group per alcohol molecule (mono-alcohol) and alcohol having a plurality of hydroxyl groups per alcohol molecule (di-alcohol, tri-alcohol, etc.), (iii) primary, secondary, and tertiary alcohol, (iv) alcohol having a terminal hydroxyl group (1-alcohol) and alcohol having a hydroxyl group in a non-terminal position (2-alcohol, 3-alcohol, etc.), and (iv) mixtures of two or more alcohol compounds, including mixtures of alcohol compounds having different values of n.

The term "long chain alcohol" means a class of saturated, primary, mono-alcohol compounds having (i) the form of a single unbranched chain which includes four or more carbon atoms, the chain beginning with a first terminal carbon atom and ending with a second terminal carbon atom, (ii) each of the chain's non-terminal carbon atoms tetravalently bound to two nearest-neighbor hydrogen atoms and to two nearest-neighbor carbon atoms of the chain, and (iii) a sole hydroxyl group, the sole hydroxyl group and two hydrogen atoms each being directly bound to the first terminal carbon atom, the second terminal carbon atom being directly bound to three hydrogen atoms (namely: normal, $C_{4+}$, saturated, primary, mono-, 1-alcohol). Typically, the number of carbon atoms in the single unbranched chain is in the range of from 5 to 21, more typically in the range of from 5 to 15, e.g., in the range of from 6 to 12.

The term "alkane" means substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes.

The term "unsaturate" or "unsaturated hydrocarbon" mean a $C_{2+}$ hydrocarbon containing at least one carbon atom directly bound to another carbon atom by a double or triple bond. The term "olefin" means an unsaturated hydrocarbon containing at least one carbon atom directly bound to another carbon atom by a double bond. In other words, an olefin is a compound which contains at least one pair of carbon atoms, where the first and second carbon atoms of the pair are directly linked by a double bond.

The term "Periodic Table" means the Periodic Chart of the Elements, as it appears on the inside cover of The Merck Index, Twelfth Edition, Merck & Co., Inc., 1996.

The term "reaction zone" or "reactor zone" means a location within a reactor, e.g., a specific volume within a reactor and/or a specific volume between two reactors for carrying out a reaction which produces alcohol. The term "fixed bed catalytic reactor" means a catalytic reactor having at least one bed of catalyst, wherein the catalyst is substantially retained within the bed and remains in a substantially fixed location within the bed.

The term "selectivity" refers to the production of a specified compound in a catalytic reaction. As an example, the phrase "the reaction has a 100% selectivity for 1-alcohol" means that the reaction produces 100% 1-alcohol. When used in connection with a specified reactant, the term "conversion" means the amount of the reactant consumed in the reaction. For example, when the specified reactant is CO, 100% conversion means 100% of the CO is consumed in the reaction.

A templated active material is one deriving structure from at least one structure-directing agent, typically called a "template". Templated active materials which contain at least some template used during active material synthesis, and or fragments thereof (atomic and/or molecular) are within the scope of the invention, although typically the templated active material contains ≤1 wt. % of template or fragments thereof based on the weight of the active material, e.g., ≤0.1 wt. %, such as ≤0.01 wt. %.

Certain aspects the invention relate templated active materials having structure derived from at least one inorganic template, e.g., from an ordered mesoporous siliceous material, or from at last one organic templating agent, e.g., from surfactant. These aspects will now be described in more detail. The invention is not limited to these aspects, and this description is not meant to foreclose other aspects within the broader scope of the invention.

Templated Active Material

The templated active material is multi-metallic in that it comprises first and second metals ($M_1$ and $M_2$). $M_1$ and $M_2$ are each one or more metal selected from Groups 7-12 of the Periodic Table. Although $M_1$ and $M_2$ can each be a mixture of metals, they each typically comprise substantially one metal only. $M_1$ is not the same as $M_2$; in other words, $M_1$ comprises a different metal or different mixture of metals than does $M_2$. Typically, $M_1$ and $M_2$ are each one or more of $M_1$ includes one or more of Cu, Fe, Co, Mn, Zn, Rh, and Ru. More typically, $M_1$ comprises, consists essentially of, or consists of iron, and $M_2$ comprises, consists essentially of, or consists of copper. While not wishing to be bound by any theory or model, it is believed that the copper provides the templated active material with oxygenate synthesis functionality and the iron provides it with Fischer-Tropsch synthesis (carbon atom chain growth) functionality.

The templated active material is mesoporous in that it has a plurality of pores, the pores having an average pore size in the range of from 2 nm to 50 nm. When the templated active material is in the form of a particulate, typically each particle has a plurality of pores having an average pore size in the specified range. While not wishing to be bound by any theory or model, it is believed that an average pore size in the specified range favors the formation of relatively long chain hydrocarbonaceous oxygenate over hydrocarbonaceous oxygenate having three or fewer carbon atoms. The templated active material has an average surface area ≥50 m² per gram of templated active material. Conventional methods can be utilized for determining (i) the type, amount, electronic structure, and physical structure of templated active material components, e.g., those of $M_1$ and/or $M_2$, (ii) average pore size, (iii) average surface area, (iv) the amount of order, if any, exhibited by the plurality of pores and the boundaries thereof, and (v) templated active material morphology (including the size and shape of particles when the templated active material is at least partly in the form of particulates). For example, the amounts of $M_1$ and/or $M_2$ can be determined using energy-dispersive mapping methods disclosed in Y. Lu, et al., Applied Catalysis A: General 429-430 (2012). Templated active material morphology can be determined using SEM and TEM methods disclosed in this article. X-ray diffraction methods disclosed in this article can be used for deterring the physical structure (and phases) of metals, including $M_1$ and/or $M_2$, present in the templated active material, and can also for determining templated active material particle size. Average surface area, average pore size, and pore size distribution can be determined using $N_2$ adsorption/desorption methods disclosed in Cao, at al., J. Mater. Sci. (2009) 44:6663-6669. The amount of mesoporous order, if any, exhibited by the pores can be determined using x-ray diffraction methods disclosed in J. S. Beck, et al., J. Am. Chem. Soc., Vol. 114, No. 127, 10834-10843 (1992). Should the templated active material have insufficient mesoporous order to exhibit diffraction peaks at a scattering angle $2\theta \leq 4°$ when utilizing the x-ray scattering methods of the J. Am. Chem. Soc. article, average pore size and the amount of ordered mesoporosity (if any) can be determined using the direct HREM imaging methods disclosed in Sakamoto, et al., Nature, 408, 449-452 (2000). The electronic structure of templated active material components such as copper and iron can be determined using photoemission methods including XPS and Auger Electron Spectroscopy methods disclosed in Y. Lu et al., ChemCatChem 6, 473-476 (2014), which is incorporated by reference herein in its entirety.

Typically, the templated active material comprises $M_1$ in an amount in the range of 0.75 wt. % to 50.0 wt. %, based on the weight of the templated active material, more typically in the range of 1.0 wt. % to 10 wt. %. Typically, the amount of $M_2$ is in the range of from 0.75 wt. % to 50.0, based on the weight of the templated active material, more typically in the range of from more typically in the range of 1.0 wt. % to 10 wt. %. In certain aspects, the templated active material has an $M_1$ to $M_2$ molar ratio in the range of from 0.25 to 4, e.g., an iron to copper molar ratio in the range of from 0.25 to 4.

All or a portion of $M_1$ can be located in the templated active material, e.g., comprising a templated active material framework which separates nearest-neighbor pores ("framework $M_1$"). In certain aspects, at least a portion of $M_1$ is located on the surface of the templated active material ("surface $M_1$"), e.g., $M_1$ located at or proximate to templated active material's pore openings and/or inside the pores. $M_1$ (surface $M_1$ and/or framework $M_1$) can be, e.g., in one or more metallic phases of $M_1$ ($M_1$ atoms bound to neighboring $M_1$ atoms) and/or in one or more carbide phases such as $FeC_2$. All or a portion of the $M_2$ can be located in the templated active material, e.g., comprising a templated active material framework which separates nearest-neighbor pores ("framework $M_2$"). In certain aspects, at least a portion of $M_2$ is located on the surface of the templated active material ("surface $M_2$"), e.g., $M_2$ located at or proximate to templated active material pore openings and/or inside the pores. $M_2$ (surface $M_2$ and/or framework $M_2$) can be, e.g., in one or more metallic phases (e.g., copper atoms bound to neighboring copper atoms) and/or in one or more carbide phases, such as $CuC_2$. Typically, the metallic and carbide phases of $M_1$ and/or $M_2$ are substantially crystalline (e.g., substantially polycrystalline), but this is not required. Typically, ≥50.0 wt. % of $M_1$ is framework $M_1$, e.g., ≥75.0 wt. %, based on the weight of the templated active material, such as ≥90.0 wt. %, or in the range of from 50.0 wt. % to 100.0 wt. %, or 75.0 wt. % to 99.0 wt. %. Typically, ≥50.0 wt. % of $M_2$ is surface $M_2$, e.g., ≥75.0 wt. %, based on the weight of the templated active material, such as ≥90.0 wt. %, or in the range of from 50.0 wt. % to 100.0 wt. %, or 75.0 wt. % to 99.0 wt. %.

When $M_1$ is iron and $M_2$ is copper, or vice versa, the templated active material can further comprise additional materials, e.g. additional metal ($M_3$). When present, the amount of $M_3$ is ≤10.0 wt. %, e.g., in the range of about 0.1 wt. % to about 10.0 wt. %, or about 0.5 wt. % to about 5 wt. %. $M_3$ can be a mixture of metals, and can include, for example, one or more of Mn, Zn, Rh, and Co. $M_3$ can be located on the templated active material surface (on internal and/or external surfaces as "surface metal"). Instead or in addition, $M_3$ can be located in the templated active material's framework ("framework metal"). Besides or in addition to $M_3$, the templated active material can further comprise other material, such as carbon (including surface carbon and/or framework carbon), e.g., carbon introduced during synthesis of a templated active material precursor. Carbon can also accumulate on the precursor and/or templated active material during precursor processing, e.g., when the templated active material is produced from the precursor by exposing the precursor to reducing conditions in the presence of a reducing agent such as syngas. Carbon can also accumulate on the templated active material when it is present during the conversion of a carbon monoxide+molecular hydrogen mixture to oxygenate. When the templated active material includes carbon, the templated active material typically comprises ≤95 wt. % carbon, based on the weight of the templated active material, e.g., ≤90 wt. %, such as in the range of from 1 wt. % to 90 wt. %, or 10 wt. % to 85 wt. %. When present, the carbon is typically in the form of one or more of (i) carbonaceous deposits, such as coke and/or soot deposits, (ii) carbonaceous layers, e.g., graphitic carbon layers, and (iii) metal carbide, e.g., $FeC_2$, $CuC_2$, etc. When present, coke/soot deposits and carbonaceous layers are typically located on and/or in the templated active material, e.g., in templated active material pores, e.g., as coke particles. When present, metal carbides can be located on and/or in the templated active material, e.g., as carbide particulates on the templated active material surface and/or in the templated active material pores. Metal carbide can also be a component of the templated active material framework, e.g., when the templated active material framework comprises iron.

The templated active material comprises ≤1.0 wt. % of oxide of $M_1$ and ≤1.0 wt. % of oxide of $M_2$. Typically, the templated active material comprises ≤0.5 wt. % of oxide of $M_1$ and/or ≤0.5 wt. % of oxide of $M_2$, e.g., ≤0.1 wt. % of oxide of $M_1$ and/or ≤0.1 wt. % of oxide of $M_2$, such as in the range of 0.05 wt. % of oxide of $M_1$ to 1.0 wt. % of oxide of $M_1$ and/or in the range of 0.05 wt. % of oxide of $M_2$ to 1.0 wt. % oxide of $M_2$. In certain aspects, the templated active material is substantially free of any oxide of $M_2$ (e.g., CuO, $Cu_2O$, etc.) and/or substantially free of any oxide of $M_1$ (e.g., $Fe_3O_4$, $Fe_2O_3$, etc.). The term "substantially free" in this context means ≤0.05 wt. % based on the weight of the templated active material. When the templated active material is produced from one or more precursors which contain oxides of $M_1$ and/or oxides of $M_2$, the method for producing the templated active material from the precursor typically includes a step for reducing these oxides, e.g., by exposing the precursor to a reducing gas such as syngas under conditions effective for reducing the templated active material. Typically, the templated active material comprises ≤15.0 wt. % of oxygen atoms, based on the weight of the templated active material, whether as unbound oxygen ions, oxygen atoms bound to at least one other oxygen atoms, oxygen atoms bound to at least one hydrogen atoms, and/or oxygen atoms bound to at least one of $M_1$ (e.g., oxide of iron) and $M_2$ (oxide of copper). More typically, the templated active material comprises ≤10.0 wt. % of oxygen atoms, e.g., ≤1.0 wt. %, such as in the range of 0.1 wt. % to 10.0 wt. %, or 0.5 wt. % to 5.0 wt. %.

The templated active material comprises a plurality of pores having an average pore size in the range of from 2 nm to 50 nm; and an average surface area ≥50 $m^2/g$. Typically, the average pore size is in the range of from 4 nm to 25 nm, and the average surface area is in the range of from 50 $m^2/g$ to 350 $m^2/g$, such as from 60 $m^2/g$ to 250 $m^2/g$. Although at least some pores in the specified size range can exhibit a substantially regular order (an "ordered mesoporous templated active material"), this is not required, and in certain aspects the templated active material includes at least some disordered mesoporous templated active material, namely templated active material having few or no pores of the specified average size that are arranged in regular order. Disordered templated active materials can include non-crystalline or poorly-crystalline framework material, but typically has a substantially crystalline (e.g., substantially polycrystalline) framework. Examples of ordered mesoporous materials appear in F. Jiao, et al., J. Mater. Chem. A, 2, 3065-3071 (2014), and examples of disordered mesoporous materials appear in the Microporous and Mesoporous Materials article. For the purpose of this description and appended claims, the terms "ordered" and "disordered" have the same meanings as used in those articles.

The templated active material can be a component of a templated active material system, e.g., one component of a templated active material composite. Besides templated active material, such a system or composite can further comprise one or more inorganic oxides, e.g., one or more of silica, alumina, magnesia, zirconia, oxide of zinc, etc. Such oxides can be present in the system as binder and/or as a support material, for example.

Templated Active Material Synthesis

The templated active material is typically synthesized using at least one structure-directing agent, typically called a "template". For example, a template can be used to produce a calcined multi-metallic templated precursor, which is then reduced to produce the templated active material. Certain synthesis methods utilizing one or more templates will now be described in more detail. The invention is not limited to these aspects, and this description is not meant to foreclose other synthesis methods within the broader scope of the invention.

Suitable templates include, e.g., (i) ordered mesoporous inorganic materials such as one or more of MCM-41, MCM-48, SBA-15, KIT-6-100, and KIT-6-40 ("hard templating") and/or (ii) carbonaceous material, e.g., hydrocarbonaceous material, such as one or more of siloxane, urea, and surfactant ("soft templating").

Producing a Calcined Multi-metallic Templated Precursor from a Hard Template

In certain aspects, the templated active material is produced from a hard template comprising oxide of silicon, e.g., MCM-41. Conventional methods can be utilized for producing the template, such as the methods disclosed in U.S. Pat. No. 6,096,288 and in J. S. Beck, et al., J. Am. Chem. Soc., Vol. 114, No. 127, 10834-10843 (1992), which are incorporated by reference herein in their entireties. A metal-substituted template is produced by substituting first metal $M_1$ and/or second metal $M_2$ for at least a portion of the silicon atoms in the template's framework. Conventional methods can be used for carrying out the substitution, such as those which include heating a synthesis mixture comprising (i) hexane, (ii) nitrate of $M_1$ and/or nitrate of $M_2$, and (iii) mesoporous silica template to a temperature of 70° C. for 20 hours. Suitable methods are disclosed in the J. Mater. Chem. A. article, which is incorporated by reference herein in its entirety. The metal-substituted template is recovered, e.g., by vacuum filtration. When the synthesis mixture comprises $M_1$ and $M_2$, the relative amount of nitrate of $M_1$ and nitrate of $M_2$ is selected is selected to achieve a molar ratio of $M_1$ to $M_2$ in the in the range of from 0.1 to 10, e.g., about 0.25 to 4.

The recovered metal-substituted template is calcined to produce a templated precursor. In aspects where only one of $M_1$ or $M_2$ is substituted for the template's framework silicon, the templated precursor is called a monometallic templated precursor. In aspects where $M_1$ and $M_2$ are substituted for the template's framework silicon, the templated precursor is called a multi-metallic templated precursor. The templated precursor is calcined, e.g., by exposing the metal-substituted template to an oxidant at a temperature ≥350° C. Conventional recovery and calcining conditions can be used, such as those disclosed in the J. Mater. Chem. A. article, but the invention is not limited thereto. Following calcination, at least a portion of any silica in the templated precursor is removed, e.g., ≥90.0 wt. % of any silica based on the weight of the templated precursor. Silica removal can be carried out by conventional methods, such as by exposing the metal-substituted template to a 2M solution of NaOH at a temperature of approximately 25° C., but the invention is not limited thereto. Suitable silica removal methods are disclosed in the J. Mater. Chem. A. article, for example.

In aspects where the templated precursor is a monometallic templated precursor comprising the first metal ($M_1$ or $M_2$ as the case may be), a multi-metallic templated precursor is produced by depositing a second metal on and/or in the monometallic templated precursor. This can be carried out, e.g., by depositing the second metal ($M_1$ or $M_2$ as the case may be) on the monometallic templated precursor's external surface and/or impregnating in the pores of the monometallic templated precursor. In certain aspects, the first metal is $M_1$, e.g., iron, and the second metal is $M_2$, e.g., copper. Typically, the amount of second metal deposited on and/or in the monometallic templated precursor is selected to achieve a molar ratio of first to second metal in the in the range of from 0.1 to 10, e.g., about 0.25 to 4. Conventional methods can be used for impregnating the second metal, e.g., by exposing the monometallic templated precursor to an impregnation solution containing nitrate of the second metal, but the invention is not limited thereto. Optionally, the impregnation solution further comprises nitrate of $M_3$ in an amount to produce a multi-metallic templated precursor of the desired $M_3$ content. Examples of suitable impregnation methods are disclosed, e.g., in J.-L. Cao, et al., J. Mater. Sci., 44, 6663-6669 (2009), which is incorporated by reference herein in its entirety. The multi-metallic templated precursor is calcined, e.g., by exposure to an oxidant at a temperature ≥350° C. Conventional calcining conditions can be used, such as those disclosed in the J. Mater. Chem. A. and J. Mater. Sci. articles. In alternative aspects, co-impregnation and/or co-deposition of the first and second metal is carried out, the relative amount of first and second metal deposited on and/or impregnated in the template is selected to achieve a molar ratio of first to second metal in the multi-metallic templated precursor in the range of from 0.1 to 10, e.g., about 0.25 to 4. Co-impregnation can simplify production of the templated active material because the second calcining step is not needed.

Producing a Calcined Multi-metallic Templated Precursor from a Soft Template

In certain aspects, the templated active material is produced from a soft template by reacting a synthesis mixture comprising at least one carbonaceous structure-directing agent and nitrate of a first metal (e.g., $M_1$ and/or $M_2$ as the case may be) to produce a mesoporous oxide template. A templated precursor is then produced by calcining the mesoporous oxide template. A multi-metallic templated precursor is produced by (i) including a nitrate of a second metal ($M_1$ or $M_2$ as the case may be) in the synthesis mixture and/or by depositing the second metal on and/or in the monometallic templated precursor, e.g., on the monometallic templated precursor's external surface and/or in the pores of the monometallic templated precursor. In certain aspects, the first metal is $M_1$, e.g., iron and the second metal is $M_2$, e.g., copper. The multi-metallic templated precursor is calcined and reduced to produce the templated active material.

The structure-directing agent is typically one or more of siloxane, polymeric glycol, urea, and surfactant, more typically surfactant. The surfactant can be an individual surfactant compound, or a mixture of individual surfactant compounds, but is typically an individual surfactant compound. The surfactant can include one or more of cationic surfactant, non-ionic surfactant, zwitterionic surfactant, and anionic surfactant, but is typically cationic. The surfactant can comprise unbranched surfactant, e.g., cetyltrimethylammonium bromide. Alternatively or in addition, the surfactant can comprise branched surfactant, such as quaternary ammonium surfactant including those having at least one alkyl spacer; oligomeric quaternary ammonium surfactant including those having (i) at least one polar spacer such as at least one hydroxyl group and/or (ii) at least one aromatic (including alkyl aromatic) spacer group; dimeric surfactant including gemini surfactant and/or dimeric surfactant which includes siloxane; trimeric surfactant including (i) polyoxyethylene ether trimeric quaternary ammonium surfactant, (ii) polyoxyethylene trimeric surfactant, (iii) ring-type trimeric surfactant, (iv) trimeric surfactant derived from amine, and (v) n-alkylphenol polyoxyethylene trimeric surfactant; tetrameric surfactant; tetrameric surfactant, including those having at least one ring spacer; star-shaped trimeric tetrameric, and hexameric quaternary ammonium surfactant, including those having at least one amide group; and tyloxopol. Conventional surfactant can be used, but the invention is not limited thereto. Certain suitable gemini surfactants are disclosed in Sakamoto, et al., Nature, 408, 449-452 (2000), which is incorporated by reference herein in its entirety. Certain suitable trimeric surfactants are disclosed in T. Yoshimura, et al., Langmuir 28, 9322-9331 (2012), which is incorporated by reference herein in its entirety.

In certain aspects, a mesoporous oxide template is produced by combining a structure-directing agent, e.g., surfactant, and nitrate of $M_1$, e.g., $Fe(NO_3)_3$, water, and optionally urea to produce a synthesis mixture. The synthesis mixture is then aged to produce mesoporous oxide template, e.g., by exposing the mixture to a temperature in the range of from about 50° C. to 150° C., at a pressure of about 1 bar (absolute) for a time in the range of about 1 hour to about 50 hours. The mesoporous oxide template can be recovered from the aged mixture, e.g., by centrifuging and washing. Suitable soft templating methods for producing the mesoporous oxide template are disclosed in Q. Liu, et al., Microporous and Mesoporous Materials, 100, 233-240 (2007), which is incorporated by reference herein in its entirety.

A mono-metallic templated precursor is then produced by calcining the mesoporous oxide template, e.g., by exposing the mesoporous oxide template to an oxidant at a temperature ≥350° C. Conventional calcining can be used, such as the calcining disclosed in the Microporous and Mesoporous Materials article, but the invention is not limited thereto.

Following calcination, a multi-metallic templated precursor is produced by depositing a second metal on and/or in the monometallic templated precursor, e.g., on the monometallic templated precursor's external surface and/or in the pores of the monometallic templated precursor. In certain aspects, the first metal is $M_1$, e.g., iron, and the second metal is $M_2$, e.g., copper. Typically, the amount of second metal deposited on and/or in the monometallic templated precursor is selected to achieve a molar ratio of $M_1$ to $M_2$ in the in the range of from 0.1 to 10, e.g., about 0.25 to 4. Conventional methods can be used for impregnating the second metal, e.g., by exposing the monometallic templated precursor to a solution containing nitrate of the second metal, but the invention is not limited thereto. Suitable impregnation methods are disclosed, e.g., in J.-L. Cao, et al., J. Mater. Sci., 44, 6663-6669 (2009), which is incorporated by reference herein in its entirety. The multi-metallic templated precursor is calcined, e.g., by exposure to an oxidant at a temperature ≥350° C. Conventional calcining conditions can be used, such as those disclosed in the J. Mater. Chem. A. article, the J. Mater. Sci. article, and in the Microporous and Mesoporous Materials article. In aspects where the synthesis mixture further comprises nitrate of the second metal (e.g., copper nitrate), the relative amount of copper nitrate and iron nitrate is selected to achieve a molar ratio of first to second metal in the multi-metallic templated precursor in the range of from 0.1 to 10, e.g., about 0.25 to 4. Utilizing a synthesis mixture comprising nitrate of $M_1$ and nitrate of $M_2$ can simplify templated active material production because the steps for impregnating the second metal and the second calcining are not needed. Optionally, the synthesis mixture further comprises nitrate of $M_3$ in an amount to produce a multi-metallic templated precursor of the desired $M_3$ content.

Producing the Templated Active Material

The templated active material is produced by reducing the calcined multi-metallic templated precursor. For example, the reduction can be carried out by exposing the calcined multi-metallic templated precursor to a reducing agent (e.g., a reducing gas such as molecular hydrogen and/or syngas) in a reactor vessel such as a tube reactor. Surprisingly, it has been found that repeated thermal treatments during processing, e.g., the calcination and reduction, do not result in templated precursor decomposition even though the templated precursor is multi-metallic. Reducing conditions can be conventional conditions for producing macroporous oxygenate synthesis catalysts from metal-substituted macroporous metal oxide, but the invention is not limited thereto. In certain aspects, the reduction is carried out under conditions which include exposing the calcined multi-metallic templated precursor to a 1:1 molar mixture of carbon monoxide and molecular hydrogen at a temperature in the range of from 200° C. to 350° C., at a pressure in the range of from 0.5 bar (absolute) to 5 bar (absolute) at a space velocity (GHSV) in the range of from 10 hr$^{-1}$ to 10,000 hr$^{-1}$, for a time in the range of about 1 hour to about 100 hours. Typically, the templated active material is maintained in a reducing environment or an inert environment until the start of the oxygenate synthesis reaction. When the maximum temperature achieved by the precursor during calcination is $T_1$, the reduction is typically carried out at a temperature $T_2$, where $T_1$ is $\geq T_2$ and $T_1-T_2$ is $\geq 10°$ C., e.g., $\geq 25°$ C., such as $\geq 50°$ C., or $\geq 75°$ C.

The templated active material is useful for producing oxygenate from carbon monoxide and molecular hydrogen. Certain aspects of the invention relating to the use of the templated active material for producing oxygenate comprising long chain alcohol will now be described in more detail. The invention is not limited to these aspects, and this description is not meant to foreclose other aspects within the broader scope of the invention.

Process for Producing Long Chain Alcohol

Certain aspects of the invention relate to a process for catalytically producing long chain alcohol by exposing a carbon monoxide+molecular hydrogen feed mixture to a catalytically effective amount of the specified templated active material under catalytic long chain alcohol synthesis process conditions. Suitable feed mixtures and process conditions will now be described in more detail. The invention is not limited to these, and this description is not meant to foreclose other process conditions within the broader scope of the invention.

The feed mixture typically comprises molecular hydrogen and ≥1 wt. % carbon monoxide, based on the weight of the feed mixture, such as ≥5 wt. %, and optionally further comprises diluent such as carbon dioxide. For example, the feed mixture can comprise 5 wt. % to 95 wt. % of carbon monoxide, and can have a molecular hydrogen molar ratio in the range of from 0.25 to 20, e.g., 0.25 to 20, such as 0.5 to 20. Such mixtures are typically referred to as synthesis gas (or "syngas"). In certain aspects, the feed mixture includes syngas comprising molecular hydrogen, ≥10 wt. % carbon monoxide, and diluent. The diluent typically comprises carbon dioxide. The syngas typically has an $H_2$:(CO+$CO_2$) molar ratio in the range of from 0.25 to 20, or 0.5 to 20, e.g., an $H_2$:CO ratio in the range of from 0.25 to 20, or 0.5 to 20. Certain suitable syngas mixtures have an $H_2$:CO molar ratio in the range of from 0.25 to 4.

The syngas can be produced from a carbon-containing source material, such as hydrocarbon, e.g., hydrocarbon in the form of one or more of natural gas, petroleum, coal, biomass, including mixtures thereof, derivatives thereof, and mixtures of such derivatives. The type of carbon-containing source material used is not critical. The source material typically comprises ≥10 vol. %, such as ≥50 vol. %, based on the volume of the source material, of at least one hydrocarbon, especially methane.

Any convenient method for producing syngas can be used, including conventional methods. Suitable methods include those described in U.S. Patent Application Publications Nos. 2007/0259972 A1, 2008/0033218 A1, and 2005/0107481, each of which is incorporated by reference herein in its entirety. For example, natural gas can be converted to syngas by steam reforming. The first step normally involves the removal of inert components in the natural gas, such as nitrogen, argon, and carbon dioxide. Natural gas liquids will also be recovered and directed to other processing or transport. The treated natural gas will comprise primarily methane and some ethane with small amounts of higher alkanes, such as propane. Preferably, the natural gas comprises more than 90 vol. % methane. The treated natural gas is then contacted with steam in the presence of a catalyst, such as one or more metals or compounds thereof selected from Groups 7 to 10 of the Periodic Table supported on at least one attrition-resistant refractory support, such as alumina. The contacting is normally conducted at high temperature, such as in the range of from 800° C. to 1100° C., and pressures ≤5000 kPa. Under these conditions, methane converts to carbon monoxide and hydrogen according to reactions, such as:

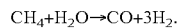

$$CH_4 + H_2O \rightarrow CO + 3H_2.$$

Steam reforming is energy intensive in that the process consumes over 200 kJ/mole of methane consumed. A second method is partial oxidation, in which the methane is burned in an oxygen-lean environment. The methane is partially-oxidized to carbon monoxide (reaction (i)), with a portion of the carbon monoxide being exposed to steam reforming conditions (reaction (ii)) to produce molecular hydrogen and carbon dioxide, according to the following representative reactions:

$$CH_4 + \tfrac{3}{2}O_2 \rightarrow CO + 2H_2O \qquad (i),$$

$$CO + H_2O \rightarrow CO_2 + H_2 \qquad (ii).$$

Partial oxidation is exothermic and yields a significant amount of heat. Because one reaction is endothermic and the other is exothermic, steam reforming and partial oxidation are often performed together for efficient energy usage. Combining the steam reforming and partial oxidation yields a third process wherein the heat generated by the partial oxidation is used to drive the steam reforming to yield syngas.

The feed mixture, typically syngas, is reacted to produce long chain alcohol in the presence of the at least one specified templated active material. Suitable process conditions will now be described in more detail.

In certain aspects, the reaction is carried out under conditions which include a reaction temperature ≥150° C., a total pressure ≥0.7 MPa (absolute), and a space velocity (GHSV) ≥50 hr$^{-1}$. Typically, the reaction conditions include a temperature in the range of from 150° C. to 300° C., e.g., 200° C. to 280° C. In certain aspects, the reaction is carried out at a temperature in the range of from 150° C. to 250° C. Total pressure is typically in the range of from 0.7 MPa to 5 MPa, such as in the range of from 1.0 MPa to 4 MPa, or 1.5 MPa to 3.5 MPa. The space velocity (GHSV) is typically in the range of from 100 hr$^{-1}$ to 10,000 hr$^{-1}$, such as in the range of from 500 hr$^{-1}$ to 5000 hr$^{-1}$. The process can be carried out in at least one reaction zone, the reaction zone being located within at least one reactor vessel, e.g., a tube reactor. The templated active material is resistant to deactivation during use, and the process can be operated continuously without interruption for catalyst regeneration, rejuvenation, or replacement for a time ≥10 hours, e.g., ≥100 hours, such as ≥1000 hours, or ≥10,000 hours.

A reaction effluent comprising long chain alcohol is conducted away from the reaction zone. Typically the reaction effluent further comprises any unreacted feed mixture components and byproducts from side reactions such as short chain alcohols. Conventional technology can be utilized for separating the long chain alcohol from the remainder of the reaction effluent, e.g., fractional distillation. If desired, other oxygenate can be produced from the long chain alcohol. For example, the process can further comprise dehydrogenating the long chain alcohol to produce corresponding aldehyde (long-chain aldehyde). The aldehyde can be converted to olefin, e.g., by removing the aldehyde's formyl group.

While the present invention has been described and illustrated with respect to certain aspects, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A process for producing oxygenate, comprising:
   (a) providing a feed mixture comprising molecular hydrogen and ≥0.01 wt. % of carbon monoxide, the feed mixture having a molecular hydrogen to carbon monoxide molar ratio in the range of from 0.01 to 100;
   (b) providing at least one templated active material, the active material comprising a first metal $M_1$, wherein $M_1$ includes at least one metal selected from Groups 7-12 of the Periodic Table;
   ≥0.5 wt. % of a second metal $M_2$, wherein (i) $M_2$ is not the same as $M_1$ and (ii) $M_2$ includes at least one metal selected from Groups 7-12 of the Periodic Table;
   ≤1.0 wt. % of oxide of $M_1$; and
   ≤1.0 wt. % of oxide of $M_2$: wherein
   the active material has an $M_2$ to $M_1$ molar ratio in the range of from 0.1 to 10, a plurality of pores having an average pore size in the range of from 2 nm to 50 nm, and an average surface area ≥50 $m^2/g$;
   (c) reacting at least a portion of the feed mixture's carbon monoxide and at least a portion of the feed mixture's molecular hydrogen in the presence of the templated active material to produce a reaction effluent comprising oxygenate, the reaction conditions including a reaction temperature ≥150° C., a total pressure ≥100 psig, and a space velocity (GHSV) ≥100 $hr^{-1}$; and
   (d) recovering at least a portion of the reaction effluent's oxygenate.

2. The process of claim 1, wherein the oxygenate comprises long chain alcohol.

3. The process of claim 1, wherein the feed mixture comprises 5 wt. % to 95 wt. % of carbon monoxide, and has a molecular hydrogen:carbon monoxide molar ratio in the range of from 0.25 to 4.

4. The process of claim 1, wherein, (i) the templated active material comprises 1.0 wt. % to 50.0 wt. % copper and 1.0 wt. % to 50.0 wt. % iron, (ii) the iron to copper molar ratio is in the range of from 0.25 to 4; (iii) the templated active material comprises is substantially free of any oxide of copper, and (iv) the templated active material comprises is substantially free of any oxide of iron.

5. The process of claim 1, wherein the average pore size is in the range of from 4 nm to 25 nm and the average surface area is in the range of from 50 $m^2/g$ to 350 $m^2/g$.

* * * * *